United States Patent [19]
Linowski et al.

[11] Patent Number: 5,822,060
[45] Date of Patent: Oct. 13, 1998

[54] METHOD OF DETECTING SAMPLE SUBSTANCES AND FLUORESCENCE SPECTROMETER USING THE METHOD

[75] Inventors: Clemens Linowski; Thomas Doerr, both of Waldbronn, Germany

[73] Assignee: Hewlett-Packard Company, Palo Alto, Calif.

[21] Appl. No.: 783,157

[22] Filed: Jan. 14, 1997

[30] Foreign Application Priority Data

Mar. 27, 1996 [EP] European Pat. Off. .............. 96104835

[51] Int. Cl.$^6$ ................................. G01J 3/30; G01J 3/28
[52] U.S. Cl. .......................... 356/318; 356/317; 356/328
[58] Field of Search ............................. 356/317, 73, 328, 356/329, 318

[56] References Cited

U.S. PATENT DOCUMENTS

| | | | |
|---|---|---|---|
| 3,637,310 | 1/1972 | Naono | ........................................ 356/309 |
| 4,353,242 | 10/1982 | Harris et al. . | |
| 4,631,687 | 12/1986 | Kowalski et al. . | |
| 4,678,917 | 7/1987 | Helms et al. . | |

FOREIGN PATENT DOCUMENTS

0437829A1  12/1990  European Pat. Off. .

*Primary Examiner*—Frank G. Font
*Assistant Examiner*—Amanda Merlino

[57] ABSTRACT

A method of detecting sample substances separated by an analytical separation technique, for example liquid chromatography or capillary electrophoresis, using electromagnetic radiation, and a corresponding fluorescence spectrometer are disclosed. The spectrometer comprises:

a flashlamp for emitting pulses of light, an adjustable diffraction element for adjusting selectable measuring wavelengths, a sample cuvette through which sample substances to be detected flow, detection means for receiving fluorescence light emitted from said sample substances flowing through said sample cuvette, and control means for adjusting different measuring wavelengths by corresponding control of said adjustable diffraction element, and for synchronizing the emission of light pulses from said flashlamp with said adjusting of different measuring wavelengths.

15 Claims, 6 Drawing Sheets

METHOD OF DETECTING SAMPLE SUBSTANCES AND FLUORESCENCE SPECTROMETER USING THE METHOD

The invention relates to a method of detecting sample substances separated by an analytical separation technique, such as liquid chromatography or capillary electrophoresis. The invention also relates to a fluorescence spectrometer using this method.

BACKGROUND OF THE INVENTION

Known techniques for detecting sample substances eluting from the separation column of a liquid chromatograph are fluorescence spectrometry and absorption spectrometry.

In fluorescence spectrometry, the sample to be analyzed is irradiated by excitation light which causes the sample substances to emit fluorescence light at characteristic wavelengths. The fluorescence light is measured by a suitable detector to derive information about the sample, in particular the composition of the sample and the quantities of the individual components present in the sample. Typically, the wavelength of the excitation light is selected by an optical component, such as a diffraction grating or a filter. The fluorescence light emitted is usually selected by a second diffraction grating or by a filter. For performing a fluorescence measurement, the grating at the excitation side of the spectrometer is set to a fixed excitation wavelength and the wavelength spectrum of the fluorescence light is recorded by means of the grating at the emission side (emission grating). The emission spectrum can be recorded for a plurality of excitation wavelengths. As an alternative thereto, the emission wavelength can be kept fixed and the excitation wavelength can be varied by corresponding adjustment of the excitation grating.

In absorption spectrometry, a beam of radiation is transmitted through the sample. The wavelengths at which the sample absorbs the radiation are characteristic for the sample substances. The radiation transmitted through the sample is spectrometrically analysed by means of a diffraction element such as a diffraction grating or a filter. The diffracted light is detected by a photosensitive element, such as a photodiode, or by an array of photodiodes. When a photodiode is used, the diffraction element is moved so that rays of different wavelengths can reach the photodiode. When an array of photodiodes is used, the diffraction element can remain stationary.

The above described spectrometric methods enable the identity of the type of a sample substance to be made from the measured spectrum by comparison with known spectra. When it is desired to determine the amount of a specific sample substance, for example in liquid chromatography, the sample concentration is measured at one specific wavelength as a function of time as the sample substances are eluting from the separation column. The corresponding graphic representation of concentration versus time is the chromatogram. Specific sample substances appear as peaks in the chromatogram. The amount of a sample substance corresponds to the area of its peak in the chromatogram. The accuracy of this measurement depends on the signal-to-noise ratio of the chromatogram. In the following, the measurements for determining the amounts of sample substances will be referred to as "quantification" measurements and the measurements for determining the type of a sample substance by spectroscopic analysis will be referred to as "qualification" measurements.

Known techniques and corresponding detectors for detecting sample substances have several limitations regarding quantification and qualification measurements. In the known detectors with a single detection element such as a photodiode or a photomultiplier tube as they are frequently used in fluorescence spectrometers, it is only possible to record a chromatogram at a specific detection wavelength. If a spectrum is to be recorded, it is required that the concentrations of the sample substances be substantially constant over a longer time interval. In liquid chromatography, however, such conditions are rarely to be found.

SUMMARY OF THE INVENTION

In view of the prior art, it is an object of the invention to provide a method of detecting sample substances using a single detection element wherein qualification measurements of the sample substances can be performed in addition to quantification measurements with negligible loss in quantification measuring accuracy.

It is a further object of the invention to provide a fluorescence spectrometer which permits measurement of excitation spectra as well as emission spectra with negligible loss in quantification measuring accuracy.

Another object is to provide a method of detecting substances eluting from the separation column of a liquid chromatograph which allows measurements of a chromatogram of the substances as well as spectra of the eluting substances without impairment of the chromatographic signal-to-noise ratio.

It is a still further object of the invention to provide a fluorescence spectrometer for use with a chromatograph which allows recording excitation spectra without impairment of the chromatographic signal-to-noise ratio.

The invention thus provides a method of detecting sample substances separated by an analytical separation technique, for example liquid chromatography or capillary electrophoresis, using electromagnetic radiation, wherein a plurality of measurements are made at a predetermined wavelength of the electromagnetic radiation at different points in time during passage of the sample substances through a detector, such as to derive quantification information indicative of the quantitative amounts of the sample substances, respectively, the method being characterized in that additional measurements are made at wavelengths different from the predetermined wavelength and at points in time other than those at which the measurements at the predetermined wavelength are made, so as to derive spectral information about the sample substances to be detected.

Using the method of the invention, it is possible to measure quantification information (e.g. chromatographic data) about the sample as well as qualification information (spectral data) even though only a single detection element is used. It is important that even though two kinds of measurements (i.e. quantification and qualification) are performed during passage of the sample through the detector, the accuracy of the quantification measurement is not impaired by the performance of the qualification measurement. The invention can also be used in connection with a photodiode array or other multichannel detector. In that case multidimensional spectra can be generated wherein an emission spectrum is recorded for each of a plurality of excitation wavelengths. It is a further advantage of the invention that it is possible to obtain spectral or multiwavelength sample information at maximum light throughput. The light is shared among quantification and qualification measurements with no light being lost for wavelength switching.

According to a further development of the invention, which is particularly useful in liquid chromatography, the qualification measurements are started in response to a trigger signal which indicates that a sample substance has entered the detector. This trigger signal can be derived from the measured quantification information.

In a preferred embodiment of the invention, the various wavelengths adjusted for deriving quantification and qualification information are adjusted by means of a rotating grating and the radiation transmitted into the sample is in the form of light pulses which are synchronized with the adjustment of the wavelengths.

A fluorescence spectrometer in accordance with the present invention comprises: a flashlamp for emitting pulses of light, an adjustable diffraction element for adjusting selectable measuring wavelengths, a sample cuvette through which sample substances to be detected flow, detection means for receiving fluorescence light emitted from said sample substances flowing through said sample cuvette, control means for adjusting different measuring wavelengths by corresponding control of said adjustable diffraction element, and for synchronizing the emission of light pulses from said flashlamp with said adjusting of different measuring wavelengths.

In a preferred embodiment of such a fluorescence spectrometer, the adjustable diffraction element is a rotating grating and a position encoder coupled to the grating is generates an output signal corresponding to its angular position. The output signal is provided to the control means for triggering the emission of light pulses from the flashlamp at defined angular positions of said grating.

BRIEF DESCRIPTION OF THE DRAWINGS

Subsequently, embodiments of the invention will be explained in detail with reference to the drawings.

DETAILED DESCRIPTION OF THE INVENTION

Figure 1:
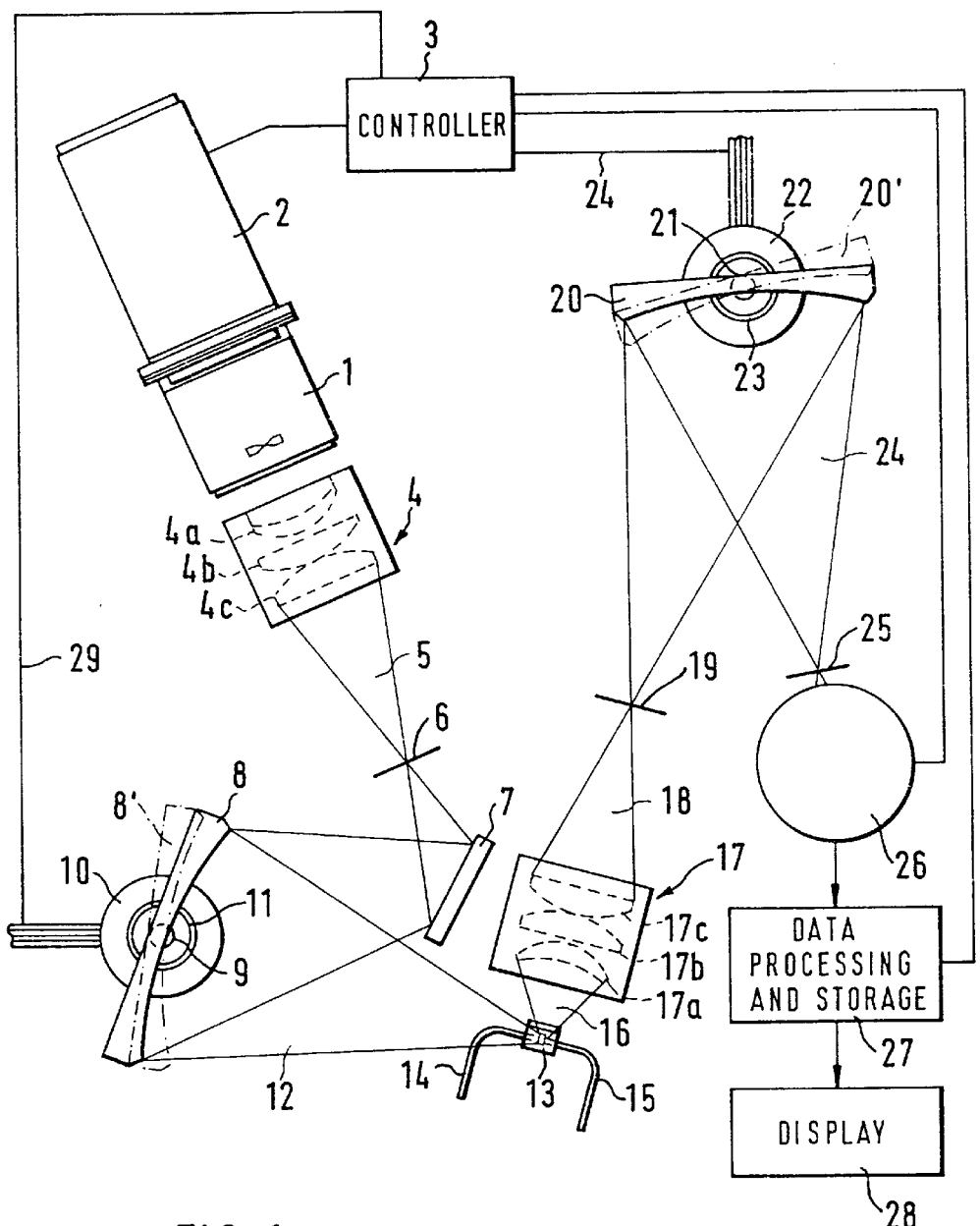
FIG. 1 is a schematic diagram of a fluorescence spectrometer according to a first embodiment of the invention.

FIG. 1 is a schematic diagram of a first embodiment of a fluorescence spectrometer according to a first embodiment of the invention. The radiation for excitation of fluorescence light is provided by a flashlamp 1, for example a bulb-type Xenon flashlight. A trigger socket 2 connected to the flashlamp 1 comprises control electronics for the flashlamp. The flashlamp is operated in a pulsed mode, with the emission of light pulses being triggered by control signals provided from a controller 3 connected to the trigger socket 2. The timing of these control signals will be explained below. Typical values of the flash frequency in the present embodiment may lie, for example, in the range between 10 and 500 Hz. Typical values of the flash duration are in the microsecond range, for example from about 0.3 to 2 microseconds.

The light emitted by the flashlamp 1 impinges on a condenser 4 which converts the ingoing light cone from the flashlamp into a converging light cone 5. In the embodiment shown, the condenser 4 consists of three lenses 4a, 4b, and 4c. The three lenses are preferably made of quartz so that light in the ultraviolet range can also be used for the excitation of fluorescence. As an alternative to the three lenses 4a–4c, a single spherical or aspherical lens or a spherical or aspherical mirror could be used. The converging light beam 5 passes through an aperture 6 and impinges thereafter on a mirror 7. The purpose of the mirror 7 is to fold the beam path so that the optical system can be arranged in a space saving manner. If the size of the spectrometer is not of importance, the mirror could be omitted. The beam reflected by the mirror 7 impinges on a focusing diffraction grating 8. The grating 8 in this embodiment is a concave holographic grating. It will also be referred to as the excitation grating.

The grating 8 is rotatable around a rotation axis 9 which is perpendicular to the plane of the paper. For the rotation of the grating 8, it is mounted to a motor 10. A rotated position of the grating is illustrated by the dotted line grating 8'. The grating can be rotated by 360 degrees. During operation of the spectrometer the grating is constantly spinning around the axis 9. A typical order of magnitude for the rotation frequency is about 80 Hz. Connected to the rotation axis 9 is a position encoder 11 which provides a signal corresponding to the instantaneous angular position of the grating 8. This signal is supplied to the controller 3 on a line 29. From this signal, the controller 3 derives control signals which are supplied to the trigger socket 2 for triggering the emission of light pulses from the flashlamp 1. The flash frequency of the flashlamp 1 is usually adjustable to the rotation frequency of the grating 8.

The grating 8 directs a converging diffracted light beam 12 into a sample cuvette 13 through which the sample to be analyzed flows. The sample enters the cuvette through an inlet tube 14 which is connected, for example, to the separation column of a liquid chromatograph. The sample leaves the cuvette 13 through an outlet tube 15. Instead of a liquid chromatograph, a capillary electrophoresis device could be connected to the inlet tube 14. In both cases, the various substances separated from each other, either by the chromatographic or by the electrophoretic separation process, are successively passing through the cuvette 13.

The excitation light 12 entering the cuvette 13 excites the sample to emit fluorescence light. The fluorescence light 16 is observed under an angle of 90 degrees with respect to the direction of the excitation light 12. The cone of fluorescence light 16 impinges on a second condenser 17 which comprises three lenses 17a, 17b, and 17c. As with the above described condenser 4, a single spherical or aspherical lens or a spherical or aspherical mirror could be used instead of the arrangement of three lenses. The beam 18 leaving the condenser 17 passes through an aperture 19 and then impinges on a second diffraction grating 20. The grating 20 will also be denoted as emission grating.

The grating 20 is rotatable around a rotation axis 21 which is perpendicular to the plane of the paper. The grating 20 is mounted to a motor 22 by means of which it can be rotated.

A rotated position of the grating 20 is illustrated by the dotted line grating 20'. A position encoder 23 connected to the axis 21 provides a signal corresponding to the instantaneous angular position of the grating 20. This signal is supplied to the controller 3 on a line 24. From this signal, the controller derives control signals which are supplied to the trigger socket 2. The excitation grating 8 and the emission grating 20 as well as the associated drive motors and position encoders have, in the present embodiment, substantially the same design.

The diffracted radiation 24 leaving the emission grating 20 is focused onto an aperture 25 and then impinges onto a photomultiplier tube 26 which provides an electrical output signal corresponding to the intensity of the radiation 24 incident on the photomultiplier 26. The output signal from the photomultiplier 26 is provided to a data processing and storage unit 27 where the data are processed in a way to be described in more detail below. The result of a measurement according to the invention is threefold:

1. a chromatogram. i.e. a representation of the amount of sample substances as a function of time;
2. fluorescence spectra, i.e., representations of the intensity of fluorescence light as a function of wavelength; and
3. fluorescence spectra as in 2., but additionally as a function of time.

The chromatogram as well as the fluorescence spectra can be displayed on a display unit 28, such as a cathode ray tube, and/or printed out by a printer. The data processing and storage unit 27 also allows to store the chromatograms and fluorescence spectra and, optionally, it may comprise an electronic library with a collection of fluorescence spectra of various substances such as to allow comparison with the measured fluorescence spectra for facilitating sample identification.

As an alternative to the photomultiplier tube 26, an avalanche diode or a CCD (charge coupled device) type detector or a micro channel plate type detector could be used.

In the following, some examples for the method of the invention which can be performed with the apparatus shown in FIG. 1 will be explained. It will be assumed in the following that either the excitation grating 8 or the emission grating 20 remains stationary during the measurement, so that either the excitation light 12 entering the cuvette 13 or the light 24 which is incident on the photomultiplier tube 26 has a fixed wavelength.

Starting with the first example, it is assumed that the emission grating 20 is at a fixed angular position such that the light detected by the photomultiplier 16 has a fixed wavelength which can be selected by a user. The excitation grating 8 is spinning around its axis 9. The generation of light pulses by the flashlamp 1 is controlled by the controller 3 in response to the angular position of the grating 8 which is detected by the position encoder 11. In that way, it is possible to generate different excitation wavelengths for successive light pulses. According to an important aspect of the invention, several measurements are made during passage of a sample substance through the flow cell 13 at a fixed wavelength for deriving a chromatogram and additional measurements are made at a plurality of different wavelengths to derive a spectrum of the sample substance in the flow cell. This is accomplished by triggering the flashlamp each time when the grating is at an angular position corresponding to the fixed wavelength and each time when the grating is at angular positions corresponding to the wavelengths constituting the spectrum, respectively.

The measuring values obtained at the fixed wavelength at different times constitute a chromatogram and the measuring values obtained during passage of a sample substance through the sample cuvette constitute a spectrum of this sample substance. The chromatogram is typically recorded over a time interval of several minutes and comprises several peaks, whereby the point in time at which a specific peak appears in the chromatogram is characteristic for the substance corresponding to this peak. A spectrum of a specific sample substance is recorded over a shorter time interval, typically in the order of seconds or smaller. A spectrum is recorded during the time of a chromatographic peak. The generation of a spectrum is preferably triggered by the appearance of a chromatographic peak, i.e., when a sample substance is actually in the flow cell. It would also be possible to record spectrum information during the entire recording of a chromatogram.

In order to illustrate the above principle, a typical time sequence of measuring points is listed below. The 71 measuring points are successively recorded, with equal time intervals between successive measuring points. The measuring points from about number 30 to about number 50 are recorded when a chromatographic peak occurs, i.e., when a sample substance flows through the cuvette. In the following table, the numbers of the measuring points are listed and the corresponding wavelength which is adjusted at this measuring point. Furthermore, it is indicated in the last column of the table if the measuring point is used for generating a chromatogram or if it is used for generating a spectrum. In the first case, the measuring point is classified as a "quantification (time)" measuring point, in the second case, it is classified as a "qualification (spectrum)" measuring point.

| measuring point (number) | wavelength | type of measuring point |
|---|---|---|
| 1–32 | 310 nm | quantification (time) |
| 33 | 300 nm | qualification (spectrum) |
| 34 | 310 nm | quantification (time) |
| 35 | 310 nm | qualification (spectrum) |
| 36 | 310 nm | quantification (time) |
| 37 | 320 nm | qualification (spectrum) |
| 38 | 310 nm | quantification (time) |
| 39 | 330 nm | qualification (spectrum) |
| 40 | 310 nm | quantification (time) |
| 41 | 340 nm | qualification (spectrum) |
| 42 | 310 nm | quantification (time) |
| 43 | 350 nm | qualification (spectrum) |
| 44 | 310 nm | quantification (time) |
| 45 | 360 nm | qualification (spectrum) |
| 46 | 310 nm | quantification (time) |
| 47 | 370 nm | qualification (spectrum) |
| 48 | 310 nm | quantification (time) |
| 49 | 380 nm | qualification (spectrum) |
| 50–71 | 310 nm | quantification (time) |

The intensity values measured by the photomultiplier 26 at the quantification measuring points are used to form a chromatogram, i.e., the values at the points 1–32, 34, 36, 38, 40, 42, 44, 46, 48, and 50–71. The intensity values correspond to the concentration values for the sample in the sample cuvette. The chromatogram can be used to determine the amounts of sample substances by determining the areas of the peaks in the chromatogram, respectively. This is the reason why the measuring points are denoted as "quantification measuring points". The intensity values at the measuring points 33, 35, 37, 39, 41, 43, 45, 47, and 49 are used to form a spectrum of the sample substance corresponding to the peak in the chromatogram. In the present example, a spectrum in the wavelength range from 300–380 nm is obtained with the measuring points being 10 nm apart from each other. During the time when the chromatographic peak occurs (measuring points 30–50), quantification and qualification measuring points are recorded in an alternating manner so that after each quantification measuring point (at 310 nm) a qualification measuring point is recorded. As explained above, this is accomplished by appropriate timing of the emission of the light pulses in relation to the angular position of the grating. The result of the measurement are a chromatogram and a spectrum which can be stored and displayed by the units 27 and 28. If there are several peaks in the chromatogram (corresponding to several sample substances), there will be a different spectrum for each peak.

In order to take into account the intensity variation in a chromatographic peak, a normalization procedure can be applied as follows:

The values at the qualification measuring points are normalized by dividing these values by the values at the quantification measuring point immediately before the qualification measuring point, respectively. In the present example, the following normalized qualification values are obtained:

at 300 nm (value at point 33)/(value at point at 32)
at 310 nm (value at point 35)/(value at point 34)
at 320 nm (value at point 37)/(value at point 36)
at 330 nm: (value at point 39)/(value at point 38)
at 340 nm: (value at point 41)/(value at point 40)
at 350 nm: (value at point 43)/(value at point 42)
at 360 nm: (value at point 45)/(value at point 44)
at 370 nm (value at point 47)/(value at point 46)
at 380 nm: (value at point 49)/(value at point 48)

Instead of dividing by the values at the quantification measuring point immediately before the qualification measuring point, one could also divide by the value at the quantification measuring immediately after the qualification measuring point, or one could use the mean value of both divisions. If the time for acquiring a spectrum is very short as compared to the duration of the chromatographic peak, a normalization is not necessary.

With the method of the invention as described before, the measuring values in the areas of the chromatogram where no sample peaks occur, i.e., in the noise area, are the same as with prior art methods for recording a chromatogram. In the area of a sample peak some values are lost as compared to prior art methods because quantification as well as qualification measuring points are recorded, but it has turned out that this has only a small effect on the peak area reproducibility. The quantification accuracy is nearly the same as with prior art chromatographic measurements using single wavelength detection, whereas the substantial advantage results that spectral information for qualification of the sample is acquired.

In a practical example of the invention, the time interval between successive measurements is 12.5 milliseconds, corresponding to a frequency of the grating rotation of 80 Hz. In a typical high performance liquid chromatographic analysis, the smallest peak width (time interval at half height of the chromatographic peak) is about 1 second. Thus, if the measurement of qualification values starts at the half height of the chromatographic peak, at least 80 data points are measured. If half of them are used for chromatographic (quantification) measurement and half of them for spectrum measurements, at least 40 points are available for spectrum measurement. For example, it is possible to measure from 300 nm to 456 nm every 4 nm one point for recording a spectrum of the sample. The measurement of qualification values may also start earlier than at the half height of the chromatographic peak: If the spectrum measurement starts at one quarter of the peak height, about 60 values for spectrum measurement can be obtained for a peak width of 1 second. The peak width of most chromatographic peaks is substantially greater than 1 second so that a large number of measuring values, chromatographic and spectral measuring values, can be recorded, allowing accurate quantification as well as qualification of the sample.

As already mentioned, the recording of measuring values of qualification (spectrum) measuring values is only started when actually a sample peak occurs in the chromatogram. The trigger point for starting the qualification measurement can be generated in one of several ways.

According to a first alternative, the trigger point is calculated by the data processing and storage unit 27 using the chromatographic data. The trigger point can be generated when the chromatographic measuring values become larger than a predetermined threshold level, indicating that the rising slope of a peak occurs.

Alternatively, a derivative threshold which is intelligent and can recognize the start of a sample peak could be used. The trigger point is generated if the slope of the chromatographic measuring curve becomes larger than a predefined value.

In a still further embodiment, the trigger time may simply be set by the user.

If the retention times of the sample peaks are rather constant, the trigger point for starting the acquisition of spectral data can simply be generated by a timetable which contains the retention times for the substances to be analyzed and initiates the data acquisition at these times, respectively.

The use of a trigger for starting spectrum data acquisition has the advantage that only the measuring values of interest are recorded so that the amount of data which have to be handled by the data processing unit is minimized.

In the following, some variations to the above described method will be explained. In the method described above, a measurement at a fixed wavelength (FIX) for quantification is followed by a measurement at a wavelength for qualification. An example of the time sequence of the measuring points would thus look as follows:

( ..., FIX, 300 nm, FIX, 310 nm, FIX, 320 nm, FIX, 330 nm, FIX, 340 nm, ... ).

In cases where a better chromatographic signal is required, it is possible to make two subsequent measurements at the fixed wavelengths. The corresponding time sequence of the measuring points would thus be as follows:

( ..., FIX, FIX, 300 nm, FIX, FIX, 310 nm, FIX, FIX, 320 nm, ... )

In cases where more spectrum information is required, it is possible to make two successive spectrum measurements before a quantification measurement at the fixed wavelength. The corresponding time sequence is:

( ..., FIX, 300 nm, 310 nm, FIX, 320 nm, 330 nm, FIX, 340 nm, 350 nm, FIX, 360 nm, 370 nm, ... ).

According to a further alternative, one can measure the spectrum data at each wavelength more than once. In that way, an improved data filtering and increased reproducibility is achieved. A possible time sequence is:

( ..., FIX, 300 nm, FIX, 300 nm, FIX, 310 nm, FIX, 310 nm, FIX, 320 nm, ...)

Another, even better possibility is:

( ..., FIX, 300 nm, FIX, 310 nm, FIX, 320 nm, FIX, 330 nm, ..., FIX, 490 nm, FIX, 500 nm, FIX, 490 nm, FIX, 480 nm, FIX, ..., 320 nm, FIX, 310 nm, FIX, 300 nm).

The final spectrum measuring value for a specific wavelength is obtained by forming the average of the several measuring values at this wavelength. It is understood that the wavelength range of interest for generating a spectrum (in the last example: 300–500 nm) is generally dependent on the sample peak being analyzed.

In another alternative of the method of the invention, a multiwavelength chromatogram is recorded together with the spectrum data. For example, two wavelengths FIX1 and FIX2 are used for generating the chromatogram, and the generation of a spectrum is started by a trigger signal when a chromatographic peak occurs. A typical time sequence is as follows:

(..., FIX1, FIX2, FIX1, FIX2, 300 nm, FIX1, FIX2, 310 nm, FIX1, FIX2, 320 nm, FIX1, FIX2, 330 nm, ...).

Alternatively, the measurement could be made according to the following time sequence:

(..., FIX1, FIX2, FIX1, FIX2, 300 nm, FIX1, 310 nm, FIX2, 320 nm, FIX1, 330 nm, FIX2, 340 nm, FIX1, 350 nm, ...).

In that way, two independent chromatograms are produced, one chromatogram at FIX1 and another chromatogram at FIX2. This has the advantage that two normally unresolved peaks may be selectively present in either of the two chromatograms and thus can be analysed quantitatively. Furthermore, it is possible to monitor any process problems (e.g. solvent effects, spurious effects), i.e. an additional monitoring channel is provided.

In a multiwavelength chromatogram consisting of N wavelengths, the noise would increase by a factor of the square root of N relative to a chromatogram measured at a single wavelength.

Figure 2:
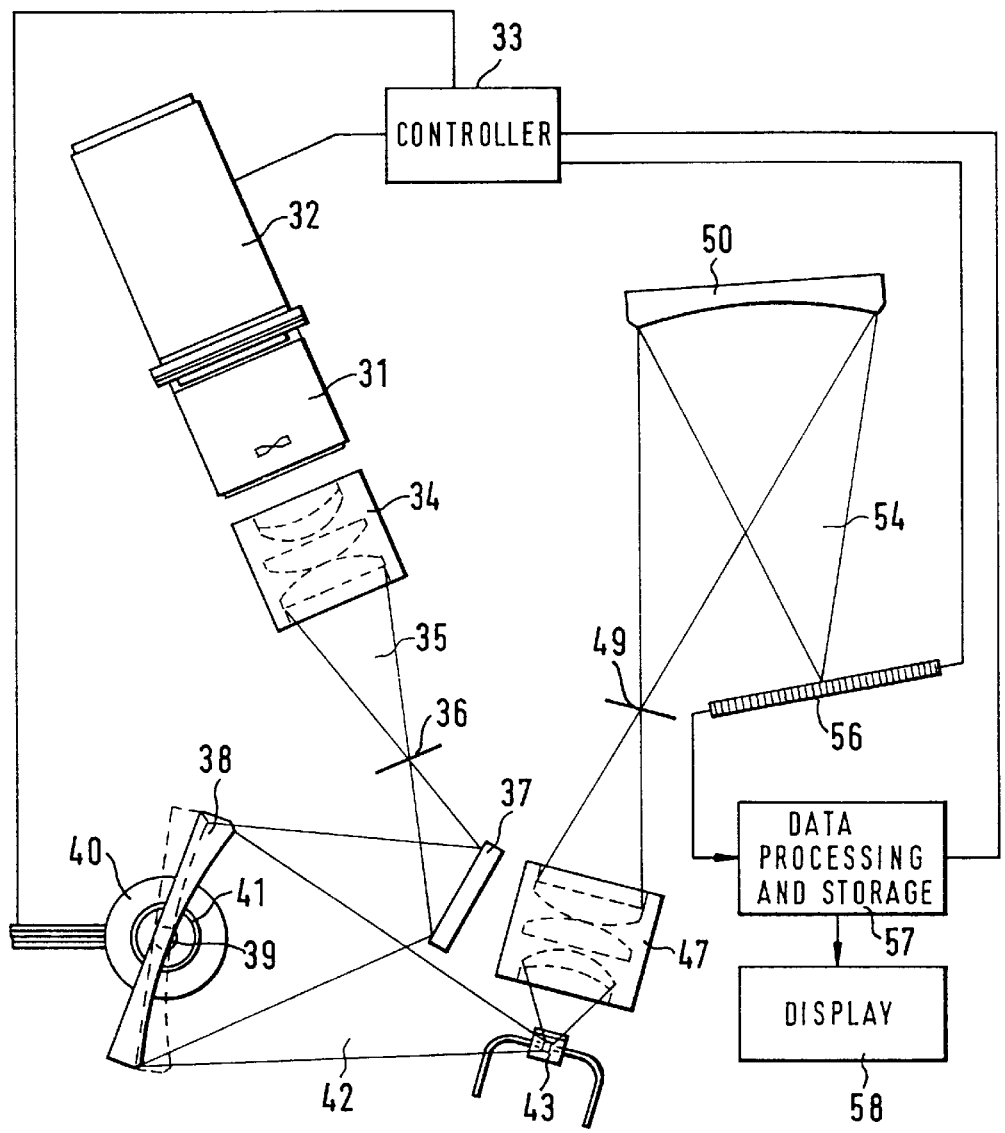
FIG. 2 is a schematic diagram of a fluorescence spectrometer according to a second embodiment of the invention.

Subsequently, a further embodiment of a fluorescence spectrometer using the invention will be described with reference to FIG. 2. The main difference to the fluorescence spectrometer shown in FIG. 1 is that a multichannel detector 56 (e.g. a photodiode array) is used instead of the photomultiplier tube 26 for detecting the fluorescence radiation and that the grating 50 is stationary. The hardware design of the remaining components is substantially the same as that of the corresponding components in FIG. 1. The flashlamp 31 connected to the trigger socket 32 provides pulses of light which pass through a condenser 34 and an aperture 36 and are directed by a mirror 37 to a diffraction grating 38. The diffraction grating 38 (excitation grating) is rotating around an axis 39, driven by a motor 40. The exit beam 42 from the grating 38 is directed into a sample cuvette 43 where it excites fluorescence light in the sample to be analyzed. The fluorescence light passes through a condenser 47 and an aperture 49 and impinges on an emission grating 50 from which a diffracted beam 54 is directed to the multichannel detector 56. The diffracted radiation leaving the emission grating 50 into the direction of the multichannel detector 56 consists of a plurality of beams of different wavelengths which are spatially separated. In FIG. 2, only one of these beams 54 corresponding to a specific wavelength is shown. The diffracted beam 54 has its focus at the position of the multichannel detector 56. A diffracted beam having a different wavelength than the beam 54 would impinge on the multichannel detector 56 at a position which is shifted parallel to the point of incidence of the beam 54, but its focus would also be at the multichannel detector 56. The grating 50 typically is a concave holographic flat field grating. The term "flat field" means that the spectral image plane of the grating is substantially flat, i.e. identical with the plane of the photosensitive elements of the multichannel detector 56.

The output signals from the multichannel detector 56 are processed and stored by a data processing and storage unit 57 and displayed by a display unit 58.

The multichannel detector 56 is preferably an array of photosensitive elements, such as photodiodes, avalanche photodiodes, multichannel plates, CCD's, etc.

With a fluorescence spectrometer using an array of photosensitive elements, a spectrum of the emitted fluorescence radiation (emission spectrum) can be recorded without requiring the rotation of the emission grating. According to the invention, the excitation grating 38 is rotating during a measurement and the flashlamp is triggered to emit light pulses at specified angular positions of the grating, corresponding to specific excitation wavelengths. The excitation wavelengths are selected as explained before in connection with FIG. 1. Thus, measuring values at one (or more) fixed wavelengths are obtained for generating a chromatogram and additional measuring values at a series of different wavelengths for spectrum information are obtained. The use of a photodiode array in connection with the invention therefore enables the generation of a multidimensional spectrum wherein an emission spectrum is recorded for each of a plurality of excitation wavelengths. Since there is spectrum information about excitation as well as about emission, the identification of sample substances is facilitated. Another advantage is that multi-injection analysis, which is a tedious and time-consuming process for any method development, is no longer necessary when using the invention. It is a further advantage that any time-programmable wavelength switching is no longer necessary because of time-resolved excitation/emission data being taken simultaneously.

The invention is not limited to fluorescence measurements, it can also be used in connection with absorption measurements. In absorption measurements, the beam of radiation is transmitted through the sample cuvette and the beam leaving the cuvette is spectrally separated by a diffraction element, typically a grating. The spectrally separated radiation then impinges on a detector. The invention is of particular advantage when the detector consists of a single photosensitive element, for example a single photodiode. In this case, the diffraction grating arranged before the detector in the optical path is spinning and the emission of light pulses from a flashlamp is triggered at specific angular positions of the grating, corresponding to specific wavelengths to be detected by the detector. As in the embodiments of the invention relating to fluorescence measurements, a fixed wavelength is selected at which quantitative measuring values are recorded to compose a chromatogram (quantification). Furthermore, measuring values are recorded at a series of different wavelengths to compose an absorption spectrum (qualification).

Figure 3:
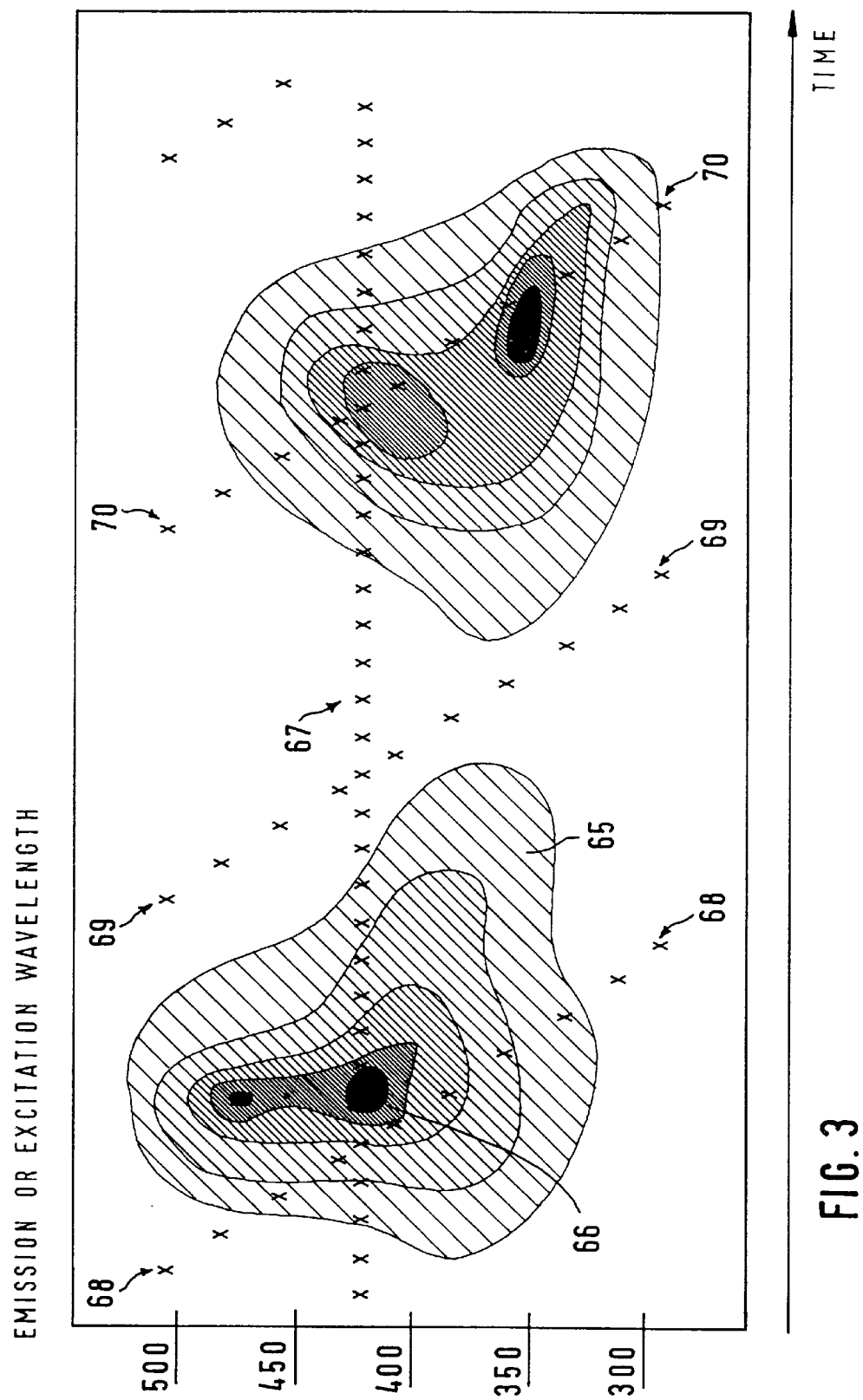
FIG. 3 is a graphical representation of a detector signal for a typical liquid chromatographic sample analysis as a function of both time and wavelength, for illustrating a schematic example of the method of the invention.

FIG. 3 is a further illustration of an example for the method of the invention. FIG. 3 schematically shows for a typical liquid chromatographic sample analysis the detector signal as a function of both time and wavelength. The horizontal axis is the time axis where the time interval since the injection of the sample into the separation column is indicated. The vertical axis is the wavelength axis at which the wavelength used for detection is indicated. In case of a fluorescence spectrometer, this wavelength can either be the emission or the excitation wavelength. In case of absorption measurements, the wavelength is the absorption wavelength. The intensity of the detector signal in the graphical representation of FIG. 3 is illustrated by different shadings of grey. The lighter areas such as area 65 depict regions of low intensity and the darker areas such as area 66 depict regions of high intensity. Thus, FIG. 3 corresponds to a threedimensional plot of intensity versus time and wavelength, also named "iso-plot".

The points characterized with "X" in FIG. 3 correspond to the measuring points at which measuring values are taken according to the method of the invention. The measuring points arranged in the horizontal line 67 are all taken at a fixed wavelength (420 nm in this example) at different times and thus constitute a chromatogram. The measuring points arranged in the inclined lines, such as line 68, 69, or 70 are taken at different wavelengths and thus constitute a spectrum, respectively. As shown in FIG. 3, the measuring points on the inclined lines 68 and 70 lie in the area of chromatographic peaks, respectively, whereas the measuring points on the line 69 lie in an area where there is substantially no measuring signal from a sample substance. Thus, for the sake of reduction of the amount of data, the measuring points on the line 69 could be also be omitted. In this case, one would use a trigger signal in the way described above for initiating the recording of spectral data only when a chromatographic peak occurs.

Figure 4:
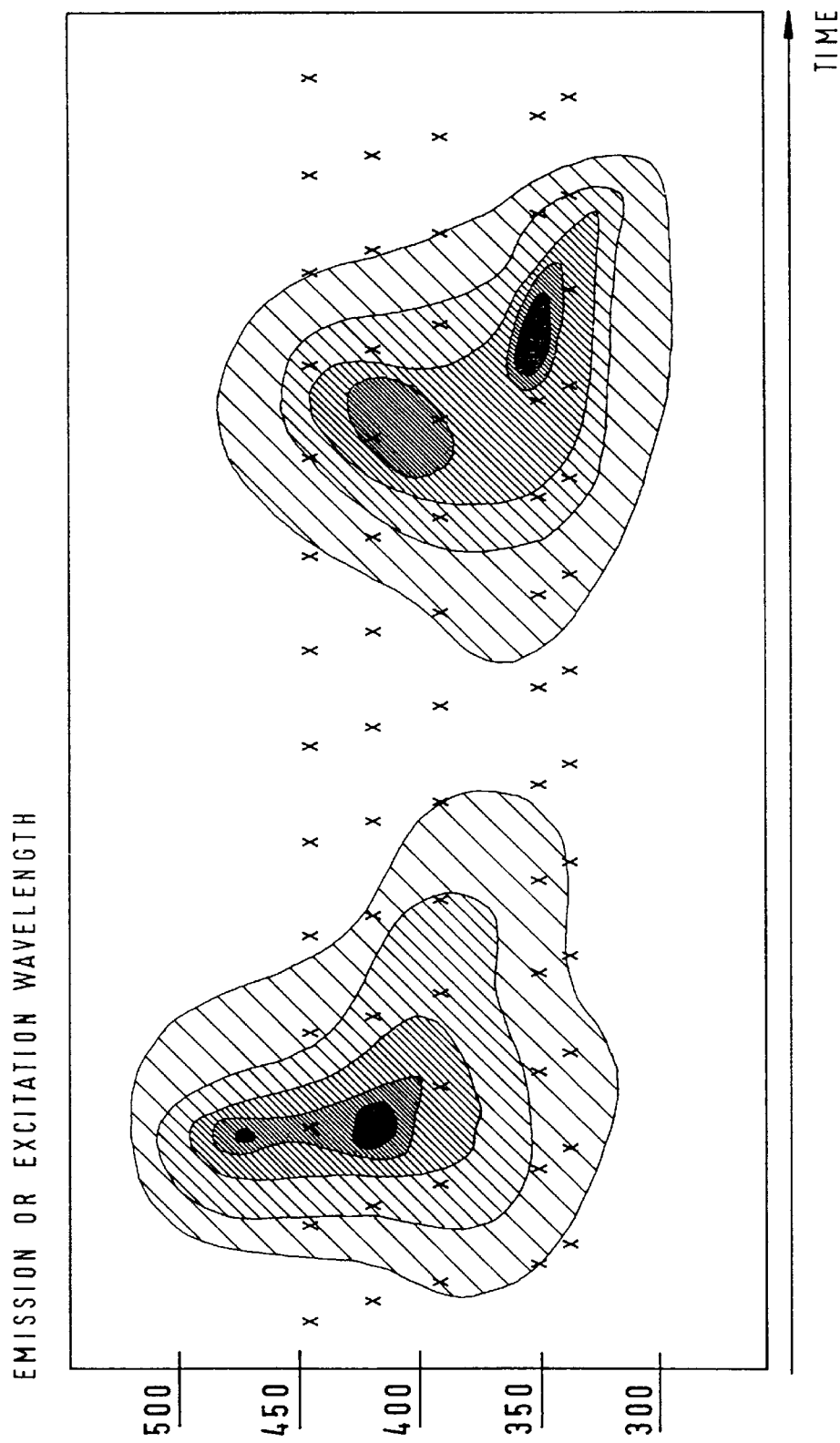
FIG. 4 is a graphical representation of a detector signal as a function of time and wavelength for illustrating a further schematic example of the method of the invention.

FIG. 4 illustrates a further example of the invention. The graphical representation is similar to the one shown in FIG. 3. The measuring points are designated with "X". In the example shown, measurements are successively and repeatedly made at five different wavelengths (340 nm, 350 nm, 390 nm, 420 nm, 440 nm) from which chromatographic as well as spectral data can be obtained.

In the following, a further example of the versatility of the method of the invention will be explained in connection with a typical chromatographic analysis. The example chosen is a chromatographic analysis of five sample substances, corresponding to five chromatographic peaks. It is assumed that the first two peaks have a peak width of about seven seconds each and that the spectral ranges of interest (fluorescence) are for the first peak from 300–550 nm and for the second peak from 350–650 nm. The three remaining peaks have a peak width of about 15 seconds each and the spectral range of interest is from 300–700 nm. It is furthermore assumed that the spectrum of the fourth peak is very similar to the spectrum of another substance so that the amount of spectral data required for this peak is higher than for the other peaks. For each of the five peaks of this particular example, the sequence of wavelengths at which measurements are made will be listed below. The listed wavelengths are those which are adjusted after the trigger signal indicating the beginning of a peak (see above) has been generated. The wavelength used for determining the area of a peak (quantification wavelength) need not necessarily be the same for all the peaks. Furthermore, there may be used more than one quantification wavelength. Thus, in the present example, the quantification wavelength for peaks 1 and 2 is 380 nm, and for the last three peaks two quantification wavelengths, 330 and 460 nm, are used.

Peak 1
  Measuring wavelengths (nm):
  380, 380, 380, 300, 380, 380, 380, 302, 380, 380, 380, 304, 380, 380, 380, 306, . . .
Peak 2
  Measuring wavelengths (nm):
  380, 380, 350, 380, 380, 352, 380, 380, 354, 380, 380, 356, 380, 380, 358, . . .
Peak 3
  Measuring wavelengths (nm):
  330, 460, 330, 460, 330, 300, 460, 330, 460, 330, 460, 302, 330, 460, 330, 460, 330, 304, 460, 330, 460, 330, 460, 306, . . .
Peak 4
  Measuring wavelengths (nm):
  330, 300, 460, 302, 330, 304, 460, 306, . . . 330, 698, 460, 700, 330, 700, 460, 698, 330, 696, 460, 694, . . . 330, 302, 460, 300, 330, 300, 460, 302, . . . , 330, 698, 460, 700
Peak 5
  Measuring wavelengths: (as peak 3)

Thus, in the sample peaks 1,2,3 and 5, the user has optimum chromatographic signal-to-noise conditions with additional spectrum information. In sample peak 4, the main interest lies in the spectrum information which is three times better than in the other peaks. The increased spectrum information is achieved at the price of a somewhat reduced peak reproducibility. It is understood that, depending on the specific chromatographic analysis, various modifications and combinations of the above described procedures are possible and that an apparatus for performing the method of the invention will typically provide the possibility to the user to select the procedures (e.g. quantification and qualification wavelength sequences) which are appropriate for his analytic problem. Alternatively, typical procedures can be pre-programmed in the data processing and storage unit.

Figure 5:
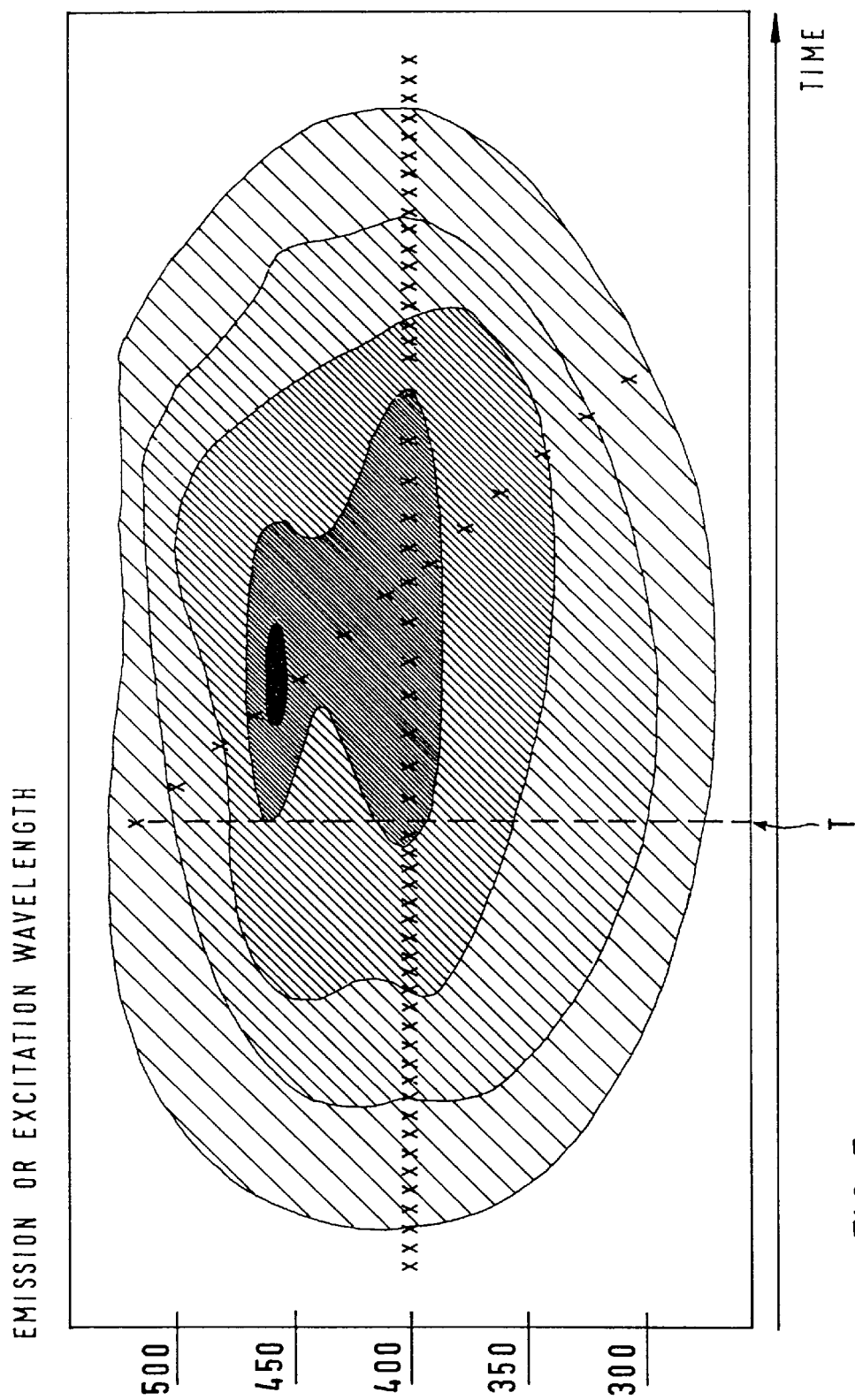
FIG. 5 is a graphical representation of a detector signal as a function of time and wavelength for illustrating a practical example of the invention.

FIG. 5 is a graphical representation similar to that in FIGS. 3 and 4, showing an example of a peak triggered spectrum. The trigger event occurs at time T. From that time on spectral data are measured (inclined line) in addition to the "chromatographic" data (horizontal line).

Figure 6A:
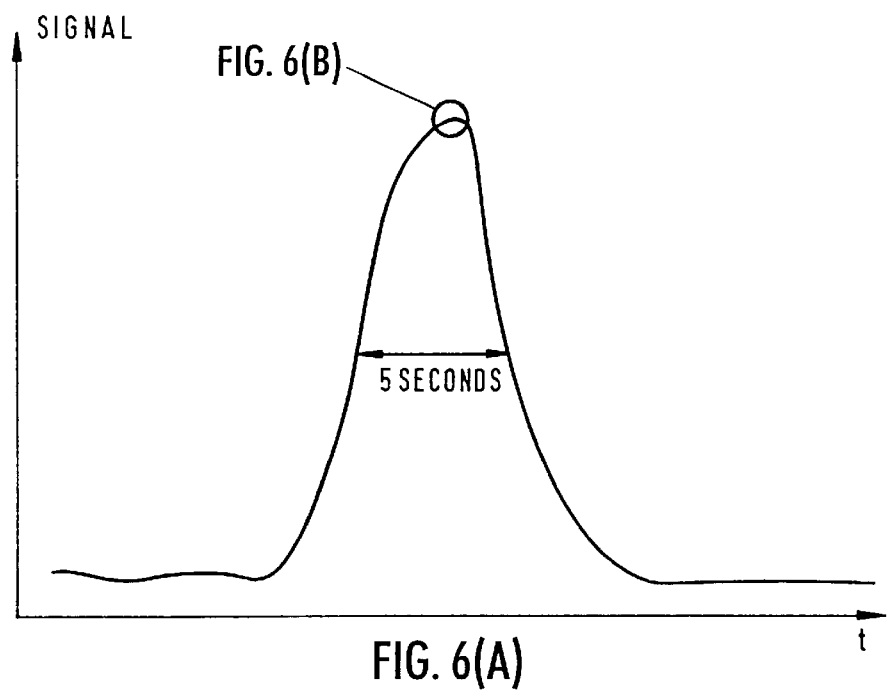
FIGS. 6(A) and 6(B) are an illustration of the principle of the invention, wherein a typical detector signal curve is depicted as a function of time as well as a magnified portion of this signal curve, showing both quantification and qualification measuring points.
Figure 6B:
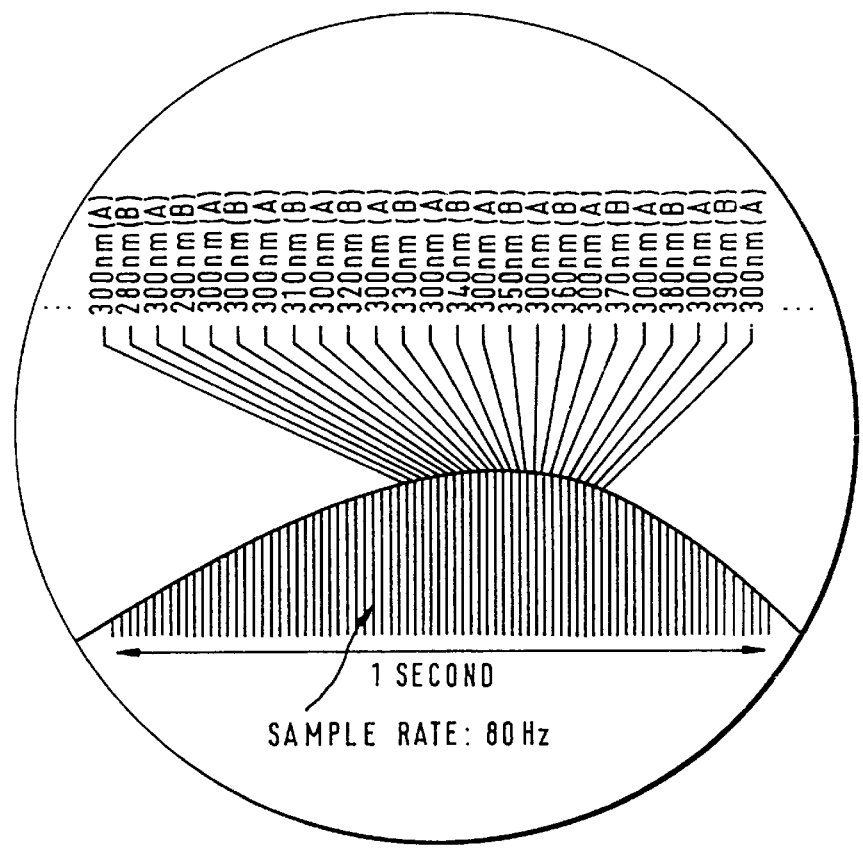

FIG. 6A and 6B is a further illustration of the principle of the invention.

FIG. 6(B) is a graphical representation of detector signal versus time, whereas 6(A) is a magnification of a portion of the measuring curve in the peak region. The magnified portion shows the individual measuring points in the peak region, with A denoting measuring points at a fixed wavelength of 300 nm and B denoting measuring points at various different wavelengths. The measuring values obtained at measuring points A are used for quantification, i.e. for producing a chromatogram, the measuring values obtained at measuring points B are used for qualification, i.e. for producing a spectrum. The time spacing of the measuring points corresponds to a sample rate of 80 Hz. The amount of measuring points shown in FIGS. 6A and 6B corresponds to an actual practical example, whereas FIGS. 3 and 4 are only schematic in this respect, since the number of measuring points ("X") shown in FIGS. 3 and 4 is smaller than the number of measurements one would usually take in practice.

The invention can also be applied in connection with a stagnant sample in the cuvette. In that case the sample is filled into the cuvette with, for example, a syringe. It is possible to record excitation versus emission spectra of the unknown sample in the cuvette in a very short time. In that way one can generate a graphical representation of the intensity as a function of excitation as well as of emission wavelength. From such a 3D plot one can derive information about the different sample components.

It is understood that the invention is not limited to the above described examples and that various modifications thereto are possible. For example, the light source may be a pulsed laser or another source which is capable of emitting pulses of radiation. A DC light source could also be used, but then the light emitted during switching from one wavelength to another will normally be lost. If, however, methods for instantaneous switching of wavelengths are used, e.g. when using acoustically tunable filters, a DC light source may be used without further disadvantages. Instead of a diffraction grating, an electrically or acoustically tunable filter or prism could be used as a diffraction element. The photosensitive elements for detecting the radiation from the sample cuvette may be, for example, avalanche photodiodes, charge coupled devices, diode arrays or intensified photodiode arrays (microchannel plates). The invention can be used in connection with liquid chromatography or capillary electrophoresis or other analytical separation methods wherein the sample substances are detected in time succession.

We claim:

1. A fluorescence spectrometer for detecting a sample substance separated by an analytical separation technique comprising:
   a flashlamp for emitting pulses of electromagnetic radiation,
   an adjustable diffraction element for adjusting selectable measuring wavelengths,
   a sample cuvette through which sample substances to be detected flow,
   an electromagnetic radiation detector arrangement for receiving fluorescence electromagnetic radiation emitted from said sample substances flowing through said sample cuvette,
   a controller for adjusting different measuring wavelengths by corresponding control of said adjustable diffraction element and for synchronizing emission of electromagnetic radiation pulses from said flashlamp with said adjusting of different measuring wavelengths,
   the adjustable diffraction element, detector arrangement, sample cuvette and controller being arranged so a plurality of measurements are made with the electromagnetic radiation detector arrangement at a predetermined wavelength of the electromagnetic radiation at different points in time while the sample substance passes through the sample cuvette to derive quantification information indicative of the quantitative amounts of the sample substance and additional measurements are made with the electromagnetic radiation detector arrangement at wavelengths different from the predetermined wavelength at points in time different from those during which the measurements at the predetermined wavelength are made to derive spectral information about the sample substances to be detected.

2. The fluorescence spectrometer of claim 1, wherein:
   the adjustable diffraction element is a rotating grating,
   a position encoder is coupled to the grating for deriving an output signal corresponding to its angular position,
   said output signal being supplied to said controller for triggering the emission of electromagnetic energy.

3. The fluorescence spectrometer of claim 2 wherein the detector arrangement comprises a photomultiplier tube.

4. The fluorescence spectrometer of claim 2 wherein the detector arrangement comprises an array of photodiodes.

5. The fluorescence spectrometer of claim 2 wherein the detector arrangement comprises a single optical receiving element.

6. The fluorescence spectrometer of claim 1 wherein the detector arrangement comprises a single optical receiving element.

7. A method of detecting a sample substance separated by an analytical separation technique using electromagnetic radiation comprising
   making, with an electromagnetic radiation detector arrangement, a plurality of measurements at a predetermined wavelength of the electromagnetic radiation at different points in time while the sample substance passes through a sample holder to derive quantification information indicative of the quantitative amounts of the sample substance; and
   making, with the electromagnetic radiation detector arrangement, additional measurements at wavelengths different from the predetermined wavelength at points in time different from those during which the measurements at the predetermined wavelength are made to derive spectral information about the sample substance to be detected.

8. The method of claim 7 further including deriving a detection signal in response to the sample substance entering said detector, said additional measurements being performed in response to the detection signal.

9. The method of claim 8 wherein said detection signal is generated from said quantification information.

10. The method of claim 8 wherein said detection signal is generated by a timetable.

11. The method of claim 7 wherein said electromagnetic radiation for said measurements is in the form of pulses of optical energy.

12. The method of claim 11 further including adjusting said wavelengths of an adjustable diffraction element at which said measurements are made.

13. The method of claim 12 wherein said adjustable diffraction element is a rotating grating, and emitting one of said light pulses each time the grating reaches an angular position corresponding to a wavelength at which quantification information or spectral information is derived.

14. The method of claim 4 wherein said analytical separation technique includes detecting the sample substance separated by the analytical separation technique of liquid chromatography and wherein said measurements comprise fluorescence measurements.

15. The method of claim 7 wherein said analytical separation technique is detecting the sample substance separated by an analytical separation technique by capillary electrophoresis and wherein said measurements comprise fluorescence measurements.

* * * * *